United States Patent
Yan et al.

(10) Patent No.: US 9,273,108 B2
(45) Date of Patent: *Mar. 1, 2016

(54) RECOMBINANT HUMAN G-CSF DIMER AND USE THEREOF FOR THE TREATMENT OF NEUROLOGICAL DISEASES

(71) Applicant: Generon (Shanghai) Corporation Ltd., Shanghai (CN)

(72) Inventors: Xiaoqiang Yan, Shanghai (CN); Zhihua Huang, Shanghai (CN); Hongzhou Yang, Shanghai (CN); Bill N. C. Sun, Shanghai (CN); Yuliang Huang, Shanghai (CN)

(73) Assignee: Generon (Shanghai) Corporation Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/014,413

(22) Filed: Aug. 30, 2013

(65) Prior Publication Data

US 2014/0004076 A1    Jan. 2, 2014

Related U.S. Application Data

(63) Continuation of application No. 13/114,035, filed on May 23, 2011, now Pat. No. 8,557,546.

(30) Foreign Application Priority Data

May 25, 2010 (CN) .......................... 2010 1 0181623

(51) Int. Cl.

| C07K 16/00 | (2006.01) |
| C07K 14/535 | (2006.01) |
| C12N 15/09 | (2006.01) |
| C12N 15/24 | (2006.01) |
| A61P 25/00 | (2006.01) |
| A61K 38/19 | (2006.01) |

(52) U.S. Cl.
CPC ............. *C07K 14/535* (2013.01); *A61K 38/193* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| 6,254,870 B1 | 7/2001 | Staten et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,797,493 B2 | 9/2004 | Sun et al. |
| 6,900,292 B2 | 5/2005 | Sun et al. |
| 7,169,905 B2 | 1/2007 | Feige |
| 7,226,759 B2 | 6/2007 | Sun et al. |
| 7,232,668 B2 | 6/2007 | Sun et al. |
| 7,307,161 B1 | 12/2007 | Jacobs et al. |
| 7,459,533 B2 | 12/2008 | Jacobs et al. |
| 7,585,646 B2 | 9/2009 | Jacobs et al. |
| 7,625,564 B2 | 12/2009 | Wang et al. |
| 7,666,402 B2 | 2/2010 | Huang et al. |
| 7,696,158 B2 | 4/2010 | Huang et al. |
| 7,718,604 B2 | 5/2010 | Huang et al. |
| 7,723,302 B2 | 5/2010 | Wu et al. |
| 7,785,601 B2 | 8/2010 | Schaebitz et al. |
| 7,972,833 B2 | 7/2011 | Dumoutier et al. |
| 8,048,984 B2 | 11/2011 | Jacobs et al. |
| 8,557,546 B2 | 10/2013 | Yan et al. |
| 2002/0142964 A1 | 10/2002 | Nissen et al. |
| 2003/0082679 A1* | 5/2003 | Sun et al. ..................... 435/69.1 |
| 2006/0153799 A1 | 7/2006 | Zhao et al. |
| 2008/0300188 A1 | 12/2008 | Yang et al. |
| 2009/0202475 A1 | 8/2009 | Abbas et al. |
| 2009/0203601 A1 | 8/2009 | Soni et al. |
| 2011/0262385 A1 | 10/2011 | Huang et al. |
| 2011/0280828 A1 | 11/2011 | Abbas et al. |
| 2012/0231065 A1 | 9/2012 | Schaebitz et al. |
| 2013/0165637 A1 | 6/2013 | Yan et al. |
| 2014/0248234 A1 | 9/2014 | Wu et al. |
| 2015/0147290 A1 | 5/2015 | Yan et al. |

FOREIGN PATENT DOCUMENTS

| CN | 1410450 A | 4/2003 |
| CN | 102260343 A | 11/2011 |
| CN | 102380090 A | 3/2012 |
| CN | 102906120 A | 1/2013 |
| EP | 2 612 676 A1 | 7/2013 |
| JP | 2003-508023 A | 3/2003 |
| JP | 2004-131507 A | 4/2004 |
| JP | 2010-531134 A | 9/2010 |
| LT | 2 010 012 A | 8/2011 |
| LT | 2 010 013 A | 8/2011 |
| WO | WO-01/03737 A1 | 1/2001 |

(Continued)

OTHER PUBLICATIONS

Aritomi et al., Nature, vol. 401:713-717, Oct. 14, 1999.*
Vidarsson et al., J Immunol., 166: 6250-6256, 2001.*
Cox et al., Experimental Hematology, 32: 441-449, Jan. 2004.*
Bowie, J.U. et al. (Mar. 16, 1990). "Deciphering the Message in Protein Sequences: Tolerances to Amino Acid Substitutions," *Science* 247(4948):1306-1310.
Burgess, W.H. et al. (Nov. 1, 1990). "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *J. Cell Biology* 111:2129-2138.

(Continued)

*Primary Examiner* — Daniel E Kolker
*Assistant Examiner* — Stacey N MacFarlane
(74) *Attorney, Agent, or Firm* — Morrison & Foerster LLP

(57) ABSTRACT

This invention relates to a recombinant human G-CSF (rhG-CSF) dimer and its use in the treatment of neurological disorder. In particular, upon ischemic neural injury in animal, this invention can be used to protect neurons with the use of rhG-CSF dimer such that function of injured nerves can be restored. Serum half-life of G-CSF dimer of this invention is prolonged and the biological activity thereof is increased.

19 Claims, 5 Drawing Sheets

(56) References Cited

FOREIGN PATENT DOCUMENTS

| WO | WO-02/29098 A2 | 4/2002 |
|---|---|---|
| WO | WO-02/36626 A1 | 5/2002 |
| WO | WO-03/076567 A2 | 9/2003 |
| WO | WO-03/076567 A3 | 9/2003 |
| WO | WO-2008/147143 A2 | 12/2008 |
| WO | WO-2008/147143 A3 | 12/2008 |
| WO | WO-2009/019441 A2 | 2/2009 |
| WO | WO-2009/019441 A3 | 2/2009 |
| WO | WO-2010/011735 A2 | 1/2010 |
| WO | WO-2010/011735 A3 | 1/2010 |
| WO | WO-2011/087986 A1 | 7/2011 |
| WO | WO-2011/147319 A1 | 12/2011 |
| WO | WO-2012/028093 A1 | 3/2012 |
| WO | WO-2013/013613 A1 | 1/2013 |

OTHER PUBLICATIONS

Cox, G.N. et al. (2004). "Enhanced Circulating Half-Life and Hematopoietic Properties of a Human Granulocyte Colony-Stimulating Factor/Immunoglobulin Fusion Protein," *Exp. Hematology* 32:441-449.
Extended European Search Report mailed on Oct. 16, 2013, for European Patent Application No. 11 786 091.6, filed on May 25, 2011, 12 pages.
Extended European Search Report mailed on Jan. 7, 2014, for European Patent Application No. 11 821119.2, filed on May 25, 2011, 26 pages.
European Office Action mailed on Sep. 4, 2014, for European Patent Application No. 11 786 091.6, filed on May 25, 2011, nine pages.
Guo, S. et al. (Nov. 2003). "Construction and Expression, Biological Activities and Protein Characteristics Analysis of Human Recombinant Bimolecular G-CSF," *Letters in Biotechnology* 14(6):489-493. (English Translation of Abstract Only).
International Search Report mailed on Sep. 8, 2011, for PCT Patent Application No. PCT/CN2011/074678, filed on May 25, 2011, 8 pages.
International Search Report mailed on Dec. 8, 2011, for PCT Patent Application No. PCT/CN2011/079143, filed on May 25, 2011, 5 pages.
Lazar, E. et al. (Mar. 1988). "Transforming Growth Factor α: Mutation of Aspartic Acid 47 and Leucine 48 Results in Different Biological Activities," *Mol. Cellular Biology* 8(3):1247-1252.
Li, Z.X. et al. (2006). "The Progress of Study on Granulocyte Colony-Stimulating Factor," *J. Int'l Neurology and Neurosurgery* 33(1):79-82 (English abstract only).
Matsueda, G.R. et al. (Oct. 1, 1979). "Increased Efficiency in Solid-Phase Edman Degradation of Synthetic Peptidyl-Resins Using an Oxymethylphenylacetamidomethyl-Linkage," *FEBS Letters* 106(1):89-92.
Schäbitz, W-R. et al. (Mar. 2003). "Neuroprotective Effect of Granulocyte Colony-Stimulating Factor After Focal Cerebral Ischemia," *Stroke* 34:745-751.
Sierra, J. et al. (Jul. 10, 2008). "A Single Dose of Pegfilgrastim Compared With Daily Filgrastim for Supporting Neutrophil Recovery in Patients Treated for Low-to-Intermediate Risk Acute Myeloid Leukemia: Results from a Randomized, Double-Blind, Phase 2 Trial," *BMC Cancer* 8:195.
Solaroglu, I. et al. (Apr. 1, 2006; e-pub. Mar. 2, 2006). "A Novel Neuroprotectant Granulocyte-Colony Stimulating Factor," *Stroke* 37(4):1123-1128.
Shyu, W.C. et al. (Mar. 28, 2006). "Granulocyte Colony-Stimulating Factor for Acute Ischemic Stroke: a Randomized Controlled Trial," *CMAJ* 174(7):927-933.
Tamada, T. et al. (Feb. 28, 2006). "Homodimeric Cross-Over Structure of the Human Granulocyte Colony-Stimulating Factor (GCSF) Receptor Signaling Complex," *PNAS* 103(9):3135-3140.
Tao, H.Z. et al. (Dec. 4-7, 2010). "F-627, a G-CSF Dimer, Stimulated a More Rapid Neutrophil Recovery in Cyclophosphamide-Treated Monkeys Compared to Monomer Rhg-CSFs," Annual Meeting of the American Society of Hematology (ASH), Orlando, FL., 2 pages.
Written Opinion of the International Searching Authority mailed on Sep. 8, 2011, for PCT Patent Application No. PCT/CN2011/074678, filed on May 25, 2011, 7 pages.
Written Opinion of the International Searching Authority mailed on Dec. 8, 2011, for PCT Patent Application No. PCT/CN2011/079143, filed on May 25, 2011, 12 pages.
Wu, C. et al. (Nov. 2007; e-pub. Oct. 14, 2007). "Simultaneous Targeting of Multiple Disease Mediators by a Dual-Variable-Domain Immunoglobulin," *Nature Biotech.* 25(11):1290-1297.
Xiao, B.G. et al. (Nov. 1, 2007). "Cell Biology and Clinical Promise of G-CSF: Immunomodulation and Neuroprotection," *J. Cellular and Molecular Medicine* 11(6):1272-1290.
Zhu, Q. et al. (Nov. 25, 2008). "Expression of rhEPO-L-Fc Fusion Protein and Analysis of its Bioactivity and Pharmacokinetics," *Chinese J. Biotech.* 24(11):1874-1879 (English translation of abstract only).
U.S. Appl. No. 12/672,274, filed Feb. 5, 2010, by Huang et al.
Donahue, J.E. et al. (2008). "Apolipoprotein E, Amyloid-β, and Blood-Brain Barrier Permeability in Alzheimer Disease," *J. Neuropathol. Exp. Neurol.* 67(4):261-270.
European Office Action mailed on May 29, 2015, for European Patent Application No. 11 821 119.2, filed on May 25, 2011, 10 pages.
European Office Action mailed on Mar. 19, 2014 for European Patent Application No. 12 817 542.9, filed on Jul. 24, 2012, three pages.
Extended European Search Report mailed on Feb. 13, 2015, for European Patent Application No. 12 817 542.9, filed on Jul. 24, 2012, five pages.
Fidler, K. et al (Mar. 2011). "The Characterization and Potential Use of G-CSF Dimers and their Pegylated Conjugates," *Acta Chim. Slov.* 58(1):1-8.
Hu, Z.T. et al. (2010). "F-627, a G-CSF Dimer, Stimulated a More Rapid Neutrophil Recovery in Cyclophosphamide-Treated Monkeys Compared to Monomer Rhg-CSFs," *Blood* 116:634 (Abstract 1485).
International Search Report mailed on Nov. 1, 2012, for PCT Patent Application No. PCT/CN2012/079106, filed on Jul. 24, 2012, 6 pages.
Nutt, J.G. et al. (Jan. 14, 2003). "Randomized, double-blind trial of glial cell line-derived neurotrophic factor (GDNF) in PD," *Neurology* 60(1)69-73.
Schneider, A. et al. (Aug. 2005; e-pub. Jul. 7, 2005). "The hematopoietic factor G-CSF is a neuronal ligand that counteracts programmed cell death and drives neurogenesis," *J. Clin. Invest.* 115(8):2083-2098.
Song, S. et al. (Jan. 7, 2011; e-pub. Oct. 14, 2010). "Granulocyte-Colony Stimulating Factor (G-CSF) Enhances Recovery in Mouse Model of Parkinson's Disease," *Neuroscience Letters* 487(2):153-157.
Tsai, K.J. et al. (Jun. 11, 2007; e-pub. May 21, 2007). "G-CSF Rescues the Memory Impairment of Animal Models of Alzheimer's Disease," *J. Exp. Med.* 204(6):1273-1280.
Written Opinion of the International Searching Authority mailed on Nov. 1, 2012, for PCT Patent Application No. PCT/CN2012/079106, filed on Jul. 24, 2012, 10 pages.

\* cited by examiner

SEQUENCE LISTING

<160> NUMBER OF SEQ ID NOS: 10

<210> SEQ ID NO 1
<211> LENGTH: 364
<212> TYPE: PRT

<213> ORGANISM: Artificial
<220> FEATURE:
<221> NAME/KEY: misc_feature
<223> OTHER INFORMATION: G-CSF dimer

<400> SEQUENCE: 1

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
                165                 170                 175

Gly Gly Gly Ser Gly Gly Gly Ser Gly Gly Gly Ser Thr Pro
            180                 185                 190

Leu Gly Pro Ala Ser Ser Leu Pro Gln Ser Phe Leu Leu Lys Cys Leu
        195                 200                 205

Glu Gln Val Arg Lys Ile Gln Gly Asp Gly Ala Ala Leu Gln Glu Lys
    210                 215                 220

Leu Cys Ala Thr Tyr Lys Leu Cys His Pro Glu Glu Leu Val Leu Leu
225                 230                 235                 240

Gly His Ser Leu Gly Ile Pro Trp Ala Pro Leu Ser Ser Cys Pro Ser
                245                 250                 255

Gln Ala Leu Gln Leu Ala Gly Cys Leu Ser Gln Leu His Ser Gly Leu
            260                 265                 270

Phe Leu Tyr Gln Gly Leu Leu Gln Ala Leu Glu Gly Ile Ser Pro Glu
        275                 280                 285

Leu Gly Pro Thr Leu Asp Thr Leu Gln Leu Asp Val Ala Asp Phe Ala
    290                 295                 300

Thr Thr Ile Trp Gln Gln Met Glu Glu Leu Gly Met Ala Pro Ala Leu
305                 310                 315                 320

Gln Pro Thr Gln Gly Ala Met Pro Ala Phe Ala Ser Ala Phe Gln Arg
                325                 330                 335

Arg Ala Gly Gly Val Leu Val Ala Ser His Leu Gln Ser Phe Leu Glu
            340                 345                 350

Val Ser Tyr Arg Val Leu Arg His Leu Ala Gln Pro
        355                 360
```

<210> SEQ ID NO 2
<211> LENGTH: 418

<210> TYPE: PRT
<213> ORGANISM: Artificial
<220> FEATURE:
<221> NAME/KEY: misc_feature
<223> OTHER INFORMATION: G-CSF dimer

<400> SEQUENCE: 2

```
Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
             20                  25                  30

Glu Lys Leu Cys Ala Thr Tyr Lys Leu Cys His Pro Glu Glu Leu Val
         35                  40                  45

Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
                165                 170                 175

Gly Gly Gly Ser Gly Gly Gly Ser Gly Gly Gly Ser Gly Gly Glu Arg
            180                 185                 190

Lys Cys Cys Val Glu Cys Pro Pro Cys Pro Ala Pro Pro Val Ala Gly
        195                 200                 205

Pro Ser Val Phe Leu Phe Pro Pro Lys Pro Lys Asp Thr Leu Met Ile
    210                 215                 220

Ser Arg Thr Pro Glu Val Thr Cys Val Val Val Asp Val Ser His Glu
225                 230                 235                 240

Asp Pro Glu Val Gln Phe Asn Trp Tyr Val Asp Gly Val Glu Val His
                245                 250                 255

Asn Ala Lys Thr Lys Pro Arg Glu Glu Gln Phe Asn Ser Thr Phe Arg
            260                 265                 270

Val Val Ser Val Leu Thr Val Val His Gln Asp Trp Leu Asn Gly Lys
        275                 280                 285

Glu Tyr Lys Cys Lys Val Ser Asn Lys Gly Leu Pro Ala Ser Ile Glu
    290                 295                 300

Lys Thr Ile Ser Lys Thr Lys Gly Gln Pro Arg Glu Pro Gln Val Tyr
305                 310                 315                 320

Thr Leu Pro Pro Ser Arg Glu Glu Met Thr Lys Asn Gln Val Ser Leu
                325                 330                 335

Thr Cys Leu Val Lys Gly Phe Tyr Pro Ser Asp Ile Ala Val Glu Trp
            340                 345                 350

Glu Ser Asn Gly Gln Pro Glu Asn Asn Tyr Lys Thr Thr Pro Pro Met
        355                 360                 365

Leu Asp Ser Asp Gly Ser Phe Phe Leu Tyr Ser Lys Leu Thr Val Asp
    370                 375                 380
```

```
Lys Ser Arg Trp Gln Gln Gly Asn Val Phe Ser Cys Ser Val Met His
385                 390                 395                 400

Glu Ala Leu His Asn His Tyr Thr Gln Lys Ser Leu Ser Leu Ser Pro
            405                 410                 415

Gly Lys

<210> SEQ ID NO 3
<211> LENGTH: 418
<212> TYPE: PRT
<213> ORGANISM: Artificial
<220> FEATURE:
<221> NAME/KEY: misc_feature
<223> OTHER INFORMATION: G-CSF dimer

<400> SEQUENCE: 3

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Ser
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly Lys Gly Ser Gly Gly Gly Ser Gly Gly Gly Gly Ser Gly
225                 230                 235                 240

Gly Gly Ser Thr Pro Leu Gly Pro Ala Ser Ser Leu Pro Gln Ser
            245                 250                 255

Phe Leu Leu Lys Cys Leu Glu Gln Val Arg Lys Ile Gln Gly Asp Gly
            260                 265                 270

Ala Ala Leu Gln Glu Lys Leu Cys Ala Thr Tyr Lys Leu Cys His Pro
            275                 280                 285

Glu Glu Leu Val Leu Leu Gly His Ser Leu Gly Ile Pro Trp Ala Pro
    290                 295                 300

Leu Ser Ser Cys Pro Ser Gln Ala Leu Gln Leu Ala Gly Cys Leu Ser
305                 310                 315                 320
```

```
Gln Leu His Ser Gly Leu Phe Leu Tyr Gln Gly Leu Gln Ala Leu
            325                 330                 335

Glu Gly Ile Ser Pro Glu Leu Gly Pro Thr Leu Asp Thr Leu Gln Leu
            340                 345                 350

Asp Val Ala Asp Phe Ala Thr Thr Ile Trp Gln Gln Met Glu Glu Leu
        355                 360                 365

Gly Met Ala Pro Ala Leu Gln Pro Thr Gln Gly Ala Met Pro Ala Phe
    370                 375                 380

Ala Ser Ala Phe Gln Arg Arg Ala Gly Gly Val Leu Val Ala Ser His
385                 390                 395                 400

Leu Gln Ser Phe Leu Glu Val Ser Tyr Arg Val Leu Arg His Leu Ala
                405                 410                 415

Gln Pro

<210> SEQ ID NO 4
<211> LENGTH: 403
<212> TYPE: PRT
<213> ORGANISM: Artificial
<220> FEATURE:
<221> NAME/KEY: misc_feature
<223> OTHER INFORMATION: G-CSF dimer

<400> SEQUENCE: 4

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Ala Ser
                165                 170                 175

Thr Lys Gly Pro Val Glu Cys Pro Pro Cys Pro Ala Pro Pro Val Ala
            180                 185                 190

Gly Pro Ser Val Phe Leu Phe Pro Pro Lys Pro Lys Asp Thr Leu Met
        195                 200                 205

Ile Ser Arg Thr Pro Glu Val Thr Cys Val Val Val Asp Val Ser His
    210                 215                 220

Glu Asp Pro Glu Val Gln Phe Asn Trp Tyr Val Asp Gly Val Glu Val
225                 230                 235                 240

His Asn Ala Lys Thr Lys Pro Arg Glu Glu Gln Phe Asn Ser Thr Phe
                245                 250                 255
```

```
Arg Val Val Ser Val Leu Thr Val His Gln Asp Trp Leu Asn Gly
            260                 265                 270
Lys Glu Tyr Lys Cys Lys Val Ser Asn Lys Gly Leu Pro Ala Ser Ile
        275                 280                 285
Glu Lys Thr Ile Ser Lys Thr Lys Gly Gln Pro Arg Glu Pro Gln Val
    290                 295                 300
Tyr Thr Leu Pro Pro Ser Arg Glu Glu Met Thr Lys Asn Gln Val Ser
305                 310                 315                 320
Leu Thr Cys Leu Val Lys Gly Phe Tyr Pro Ser Asp Ile Ala Val Glu
                325                 330                 335
Trp Glu Ser Asn Gly Gln Pro Glu Asn Asn Tyr Lys Thr Thr Pro Pro
                340                 345                 350
Met Leu Asp Ser Asp Gly Ser Phe Phe Leu Tyr Ser Lys Leu Thr Val
            355                 360                 365
Asp Lys Ser Arg Trp Gln Gln Gly Asn Val Phe Ser Cys Ser Val Met
        370                 375                 380
His Glu Ala Leu His Asn His Tyr Thr Gln Lys Ser Leu Ser Leu Ser
385                 390                 395                 400
Pro Gly Lys

<210> SEQ ID NO 5
<211> LENGTH: 403
<212> TYPE: PRT
<213> ORGANISM: Artificial
<220> FEATURE:
<221> NAME/KEY: misc_feature
<223> OTHER INFORMATION: G-CSF dimer

<400> SEQUENCE: 5

Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
                20                  25                  30
Pro Glu Val Thr Cys Val Val Val Asp Val Ser His Glu Asp Pro Glu
            35                  40                  45
Val Gln Phe Asn Trp Tyr Val Asp Gly Val Glu Val His Asn Ala Lys
        50                  55                  60
Thr Lys Pro Arg Glu Glu Gln Phe Asn Ser Thr Phe Arg Val Val Ser
65                  70                  75                  80
Val Leu Thr Val Val His Gln Asp Trp Leu Asn Gly Lys Glu Tyr Lys
                85                  90                  95
Cys Lys Val Ser Asn Lys Gly Leu Pro Ala Ser Ile Glu Lys Thr Ile
            100                 105                 110
Ser Lys Thr Lys Gly Gln Pro Arg Glu Pro Gln Val Tyr Thr Leu Pro
        115                 120                 125
Pro Ser Arg Glu Glu Met Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Met Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
```

```
His Asn His Tyr Thr Gln Lys Ser Leu Ser Leu Ser Pro Gly Lys Ala
        210                 215                 220

Ser Thr Lys Gly Pro Thr Pro Leu Gly Pro Ala Ser Ser Leu Pro Gln
225                 230                 235                 240

Ser Phe Leu Leu Lys Cys Leu Glu Gln Val Arg Lys Ile Gln Gly Asp
                245                 250                 255

Gly Ala Ala Leu Gln Glu Lys Leu Cys Ala Thr Tyr Lys Leu Cys His
                260                 265                 270

Pro Glu Glu Leu Val Leu Leu Gly His Ser Leu Gly Ile Pro Trp Ala
            275                 280                 285

Pro Leu Ser Ser Cys Pro Ser Gln Ala Leu Gln Leu Ala Gly Cys Leu
        290                 295                 300

Ser Gln Leu His Ser Gly Leu Phe Leu Tyr Gln Gly Leu Leu Gln Ala
305                 310                 315                 320

Leu Glu Gly Ile Ser Pro Glu Leu Gly Pro Thr Leu Asp Thr Leu Gln
                325                 330                 335

Leu Asp Val Ala Asp Phe Ala Thr Thr Ile Trp Gln Gln Met Glu Glu
                340                 345                 350

Leu Gly Met Ala Pro Ala Leu Gln Pro Thr Gln Gly Ala Met Pro Ala
            355                 360                 365

Phe Ala Ser Ala Phe Gln Arg Arg Ala Gly Gly Val Leu Val Ala Ser
        370                 375                 380

His Leu Gln Ser Phe Leu Glu Val Ser Tyr Arg Val Leu Arg His Leu
385                 390                 395                 400

Ala Gln Pro

<210> SEQ ID NO 6
<211> LENGTH: 413
<212> TYPE: PRT
<213> ORGANISM: Artificial
<220> FEATURE:
<221> NAME/KEY: misc_feature
<223> OTHER INFORMATION: G-CSF dimer

<400> SEQUENCE: 6

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160
```

Leu Glu Val Ser Tyr Arg Val Leu Arg His Leu Ala Gln Pro Gly Ser
                165                 170                 175

Gly Gly Gly Ser Gly Gly Gly Ser Gly Gly Gly Ser Val Glu
            180                 185                 190

Cys Pro Pro Cys Pro Ala Pro Pro Val Ala Gly Pro Ser Val Phe Leu
                195                 200                 205

Phe Pro Pro Lys Pro Lys Asp Thr Leu Met Ile Ser Arg Thr Pro Glu
            210                 215                 220

Val Thr Cys Val Val Val Asp Val Ser His Glu Asp Pro Glu Val Gln
225                 230                 235                 240

Phe Asn Trp Tyr Val Asp Gly Val Glu Val His Asn Ala Lys Thr Lys
                245                 250                 255

Pro Arg Glu Glu Gln Phe Asn Ser Thr Phe Arg Val Val Ser Val Leu
            260                 265                 270

Thr Val Val His Gln Asp Trp Leu Asn Gly Lys Glu Tyr Lys Cys Lys
            275                 280                 285

Val Ser Asn Lys Gly Leu Pro Ala Ser Ile Glu Lys Thr Ile Ser Lys
            290                 295                 300

Thr Lys Gly Gln Pro Arg Glu Pro Gln Val Tyr Thr Leu Pro Pro Ser
305                 310                 315                 320

Arg Glu Glu Met Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Met Leu Asp Ser Asp Gly
            355                 360                 365

Ser Phe Phe Leu Tyr Ser Lys Leu Thr Val Asp Lys Ser Arg Trp Gln
            370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys
                405                 410

<210> SEQ ID NO 7
<211> LENGTH: 413
<212> TYPE: PRT
<213> ORGANISM: Artificial
<220> FEATURE:
<221> NAME/KEY: misc_feature
<223> OTHER INFORMATION: G-CSF dimer

<400> SEQUENCE: 7

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile

```
            100                 105                 110
Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Gly
210                 215                 220

Ser Gly Gly Gly Ser Gly Gly Gly Ser Gly Gly Gly Ser Thr
225                 230                 235                 240

Pro Leu Gly Pro Ala Ser Ser Leu Pro Gln Ser Phe Leu Leu Lys Cys
                245                 250                 255

Leu Glu Gln Val Arg Lys Ile Gln Gly Asp Gly Ala Ala Leu Gln Glu
            260                 265                 270

Lys Leu Cys Ala Thr Tyr Lys Leu Cys His Pro Glu Glu Leu Val Leu
        275                 280                 285

Leu Gly His Ser Leu Gly Ile Pro Trp Ala Pro Leu Ser Ser Cys Pro
290                 295                 300

Ser Gln Ala Leu Gln Leu Ala Gly Cys Leu Ser Gln Leu His Ser Gly
305                 310                 315                 320

Leu Phe Leu Tyr Gln Gly Leu Leu Gln Ala Leu Glu Gly Ile Ser Pro
                325                 330                 335

Glu Leu Gly Pro Thr Leu Asp Thr Leu Gln Leu Asp Val Ala Asp Phe
            340                 345                 350

Ala Thr Thr Ile Trp Gln Gln Met Glu Glu Leu Gly Met Ala Pro Ala
        355                 360                 365

Leu Gln Pro Thr Gln Gly Ala Met Pro Ala Phe Ala Ser Ala Phe Gln
370                 375                 380

Arg Arg Ala Gly Gly Val Leu Val Ala Ser His Leu Gln Ser Phe Leu
385                 390                 395                 400

Glu Val Ser Tyr Arg Val Leu Arg His Leu Ala Gln Pro
                405                 410

<210> SEQ ID NO 8
<211> LENGTH: 174
<212> TYPE: PRT
<213> ORGANISM: Artificial
<220> FEATURE:
<221> NAME/KEY: misc_feature
<223> OTHER INFORMATION: G-CSF dimer

<400> SEQUENCE: 8

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45
```

Leu Leu Gly His Ser Leu Gly Ile Pro Trp Ala Pro Leu Ser Ser Cys
         50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 9
<211> LENGTH: 1368
<212> TYPE: DNA
<213> ORGANISM: Artificial
<220> FEATURE:
<221> NAME/KEY: misc_feature
<223> OTHER INFORMATION: G-CSF dimer coding sequence

<400> SEQUENCE: 9
aagcttccca gacccatggc tggacctgcc acccagagcc ccatgaagct gatggccctg      60
cagctgctgc tgtggcacag tgcactctgg acagtgcagg aagccacccc cctgggccct     120
gccagctccc tgccccagag cttcctgctc aagtgcttag agcaagtgag gaagatccag     180
ggcgatggcg cagcgctcca ggagaagctg tgtgccacct acaagctgtg ccaccccgag     240
gagctggtgc tgctcggaca ctctctgggc atccccctgg gctcccctga gcagctgccc     300
agccaggccc tgcagctggc aggctgcttg agccaactcc atagcggcct tttcctctac     360 cagggggctcc tgcaggccct ggaagggatc tcccccgagt ggggtcccac cttggacaca     420
ctgcagctgg acgtcgccga ctttgccacc accatctggc agcagatgga agaactggga     480
atggcccctg ccctgcagcc cacccagggt gccatgccgg ccttcgcctc tgctttccag     540
cgccgggcag gaggggtcct ggttgcctcc catctgcaga gcttcctgga ggtgtcgtac     600
cgcgttctac gccaccttgc ccagcccgga tccggtggcg gttccggtgg aggcggaagc     660
ggcggtggag gatcagagcg caaatgttgt gtcgagtgcc accgtgccc agcaccacct     720 gtggcaggac cgtcagtctt cctcttcccc ccaaaaccca aggacaccct catgatctcc     780
cggacccctg aggtcacgtg cgtggtggtg gacgtgagcc acgaagaccc cgaggtccag     840
ttcaactggt acgtggacgg cgtggaggtg cataatgcca agacaaagcc acgggaggag     900
cagttcaaca gcacgttccg tgtggtcagc gtcctcaccg ttgtgcacca ggactggctg     960
aacggcaagg agtacaagtg caaggtctcc aacaaaggcc tcccagcctc catcgagaaa    1020
accatctcca aaaccaaagg cagccccga gaaccacagg tgtacaccct gcccccatcc    1080
cgggaggaga tgaccaagaa ccaggtcagc ctgacctgcc tggtcaaagg cttctacccc    1140
agcgacatcg ccgtggagtg ggagagcaat gggcagccgg agaacaacta caagaccaca    1200
cctcccatgc tggactccga cggctccttc ttcctctaca gcaagctcac cgtggacaag    1260
agcaggtggc agcaggggaa cgtcttctca tgctccgtga tgcatgaggc tctgcacaac    1320

-continued

```
cactacacgc agaagagcct ctccctgtct ccgggtaaat gagaattc          1368
```

<210> SEQ ID NO 10
<211> LENGTH: 1353
<212> TYPE: DNA
<213> ORGANISM: Artificial
<220> FEATURE:
<221> NAME/KEY: misc_feature
<223> OTHER INFORMATION: G-CSF dimer coding sequence

<400> SEQUENCE: 10

```
aagcttccca gacccatggc tggacctgcc acccagagcc ccatgaagct gatggccctg    60
cagctgctgc tgtggcacag tgcactctgg acagtgcagg aagccacccc cctgggccct   120
gccagctccc tgccccagag cttcctgctc aagtgcttag agcaagtgag gaagatccag   180
ggcgatggcg cagcgctcca ggagaagctg tgtgccacct acaagctgtg ccaccccgag   240
gagctggtgc tgctcggaca ctctctgggc atccccctgg gctccctgag cagctgcccc   300
agccaggccc tgcagctggc aggctgcttg agccaactcc atagcggcct tttcctctac   360
caggggctcc tgcaggccct ggaagggatc tcccccgagt tgggtccc ac cttggacaca   420
ctgcagctga cgtcgccga ctttgccacc accatctggc agcagatgga agaactggga   480
atggcccctg ccctgcagcc cacccagggt gccatgccgg ccttcgcctc tgctttccag   540
cgccgggcag gagggtcct ggttgcctcc catctgcaga gcttcctgga ggtgtcgtac   600
cgcgttctac gccaccttgc ccagcccgga tccggtggcg gttccggtgg aggcggaagc   660
ggcggtggag gatcagtcga gtgcccaccg tgcccagcac cacctgtggc aggaccgtca   720
gtcttcctct tccccccaaa acccaaggac accctcatga tctcccggac ccctgaggtc   780
acgtgcgtgg tggtggacgt gagccacgaa gaccccgagg tccagttcaa ctggtacgtg   840
gacggcgtgg aggtgcataa tgccaagaca aagccacggg aggagcagtt caacagcacg   900
ttccgtgtgg tcagcgtcct caccgttgtg caccaggact ggctgaacgg caaggagtac   960
aagtgcaagg tctccaacaa aggcctccca gcctccatcg agaaaaccat ctccaaaacc  1020
aaagggcagc cccgagaacc acaggtgtac accctgcccc catcccggga ggagatgacc  1080
aagaaccagg tcagcctgac ctgcctggtc aaaggcttct accccagcga catcgccgtg  1140
gagtgggaga gcaatgggca gccggagaac aactacaaga ccacacctcc catgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
agcctctccc tgtctccggg taaatgagaa ttc                              1353
```

RECOMBINANT HUMAN G-CSF DIMER AND USE THEREOF FOR THE TREATMENT OF NEUROLOGICAL DISEASES

CROSS-REFERENCE TO RELATED APPLICATION

This application is a continuation of U.S. Ser. No. 13/114,035 filed on 23 May 2011, which claims benefit of Chinese Patent Application having Serial No. CN201010181623.5 filed 25 May 2010, which is hereby incorporated by reference herein in its entirety.

REFERENCE TO SEQUENCE LISTING

The hard copy of the sequence listing submitted herewith and the corresponding computer readable form are both incorporated herein by reference in their entireties.

FIELD OF INVENTION

This invention relates to the area of biological and medical technologies, in particular, this invention relates to a novel human G-CSF dimer and its use in the treatment of diseases associated with neural injury.

BACKGROUND OF INVENTION

Human granulocyte colony-stimulating factor (G-CSF) is a glycoprotein having 204 amino acids with 30 amino-acid signal peptides. Mature G-CSF protein, having 18-20 kDa in molecular weight, is composed of 174 amino acids without signal peptides and secreted out of the cells. Human cells mainly responsible for such secretion are monocytes, fibroblasts, and endothelial cells.

There are three main biological functions for G-CSF, namely:

1. acting on myeloid precursors and stem cells to drive the differentiation, development, and maturation of neutrophils;
2. activating mature neutrophils to participate in immune response; and
3. acting with other hematopoietic growth factors such as stem cell factor, Flt-3 ligand, and GM-CSF to mobilize hematopoietic stem cells.

G-CSF receptor (G-CSFR) is proven to exist in bone marrow hematopoietic stem cells Sca$^+$Lin$^-$Thl$^{low}$, precursor cells CD34$^+$, committed granulocyte precursor cells, and mature neutrophils. G-CSFR is a specific receptor having a high affinity to G-CSF and 812 amino acids.

Tamada et al. obtained the crystalline structure of the G-CSF:G-CSFR complex and the stoichiometry of G-CSF:G-CSFR complex was shown as a 2:2 ratio by the 2.8 angstrom diffraction analysis (PNAS, 2008, Vol. 103: 3135-3140). In other words, in each complex, each G-CSF binds to one receptor chain to form a G-CSF-receptor complex when two G-CSF-receptor complexes are brought to close proximity, a 2:2 dimer is formed as a result of this interaction. Under this circumstance, the carboxyl terminal of the G-CSF receptor is then able to activate the downstream signal molecules JAKs (Janus tyrosine kinases, primarily JAK2). Consequently, JAK2 actives STAT3 to switch on the transcriptional genes which are critical for neutrophil differentiation and proliferation and activation.

In 2003, Schabitz W. R. et al. reported that recombinant human G-CSF (rhG-CSF) was shown to have a protective functionality on nerve cells from the study on the ischemic animal model (Storke, 2003, 34; 745-751). Later in 2006, Shyu et al. reported that rhG-CSF was shown to have clinical efficacy in the treatment of patients having acute stroke in which the patients were administrated with rhG-CSF daily for five consecutive days (CMAJ, 2006, 174:927-933). The in vivo half-life of rat G-CSF upon subcutaneous administration is about 2 hours, whereas the half-life of human G-CSF upon subcutaneous administration is only 3.5 hours. Therefore, it is required to administrate patients in need thereof with the drug daily, or intravenous infusion and this will affect the living quality of patients.

SUMMARY OF INVENTION

In the light of the foregoing background, it is an object of the present invention to provide an alternate drug for the treatment of diseases associated with neural injury with improved efficacy and the manufacture thereof.

Accordingly, the present invention, in one aspect, is a G-CSF dimer of formula (I):

$$M1\text{-}L\text{-}M2 \qquad (I)$$

wherein M1 is a first monomer of G-CSF; M2 is a second monomer of G-CSF; and L is a linker connecting said first monomer and said second monomer and disposed there between.

Also, the G-CSF dimer retains the biological activity of G-CSF monomer and has a serum half-life of longer than twice of that of either the first or said second monomer.

In an exemplary embodiment of the present invention, the L is selected from the group consisting of:
  a). an organic linker;
  b). a short peptide comprising 3 to 50 amino acids; and
  c). a polypeptide of formula (II):

$$-\text{Z}-\text{Y}-\text{Z}- \qquad (II)$$

wherein Y is a carrier protein; Z is a short peptide(s) comprising 0 to 30 amino acids. In an exemplary embodiment, the short peptide without any amino acid refers to a peptide bond.

In yet another exemplary embodiment, the linker has sufficiently little steric hindrance to the G-CSF dimer such that the proper fold and conformation formed by the configuration of the first monomer and the second monomer is not affected or significantly affected.

In one exemplary embodiment, the organic linker is selected from a group consisting of oxymethylphenylacetamidomethyl (PAM) resin, 4-oxymethyl phenylacetamidomethyl resin, and chloromethyl polystyrene resin.

In another exemplary embodiment, the first monomer and the second monomer are of the same entity.

In an exemplary embodiment, the biological activity of the fusion protein includes:
  a). acting on neutrophil granulocytes and stem cells to drive the differentiation, growth, and maturation of neutrophils; and
  b). activating mature neutrophils to participate in immune response.

In another exemplary embodiment, the carrier protein is albumin or Fc fragment of human IgG.

In one exemplary embodiment, the serum half-life of the G-CSF dimer is more than three, five, or ten times of that of the first and/or the second monomer.

In another exemplary embodiment, the G-CSF dimer is produced by two G-CSF-Fc complexes in which each G-CSF-Fc complex comprises an amino acid sequence selected from a group consisting of SEQ ID NO: 2-7.

In yet another aspect of the present invention, a fusion protein made of a first polypeptide and a second polypeptide is provided in which the first and second polypeptides comprises an amino acid sequence of SEQ ID NO:8, and the two polypeptides are linked together without steric hindrance.

In one exemplary embodiment, the first and second polypeptides are G-CSF monomers.

In another exemplary embodiment of the present invention, the linking without hindrance between said first polypeptide and the second polypeptide is carried out by a linker. In this embodiment, the linker is:

a). an organic linker with sufficiently little steric hindrance for not affecting or significantly affecting the proper fold and conformation formed by the configuration of said first monomer and said second monomer;

b). a short peptide comprising 3 to 50 amino acids; and c). a polypeptide of formula (II):

—Z—Y—Z—    (II)

wherein Y is a carrier protein; Z is a short peptide(s) comprising 0 to 30 amino acids. In an exemplary embodiment, the short peptide without any amino acid refers to a peptide bond.

In one exemplary embodiment, the organic linker is: oxymethylphenylacetamidomethyl (PAM) resin, 4-oxymethyl phenylacetamidomethyl resin, and chloromethyl polystyrene resin.

In another aspect of the present invention, a pharmaceutical composition is provided comprising as its active ingredient, a purified G-CSF dimer produced by two G-CSF-Fc complexes in which each G-CSF-Fc complex comprises an amino acid sequence selected from a group consisting of SEQ ID NO: 2-7. In an exemplary embodiment, the G-CSF dimer has a purity of 90-100%; in another exemplary embodiment, the G-CSF dimer has a purity of 95-100%; in yet another exemplary embodiment, the G-CSF dimer has a purity of 99-100%.

In one exemplary embodiment in this specific aspect, a method to treat a neurological disorder comprising administrating an effective amount of the aforesaid pharmaceutical composition to a subject in need of the treatment. In an exemplary embodiment, the effective amount ranges from 0.001-1,000 mg of the dimer per dose. In yet another exemplary embodiment, disease is selected from a group consisting of: stroke, spinal injury, and neurological disorders accompanied with blood brain barrier injury.

In another exemplary embodiment in this specific aspect, a method of activating STAT3 in neural cells comprising administering an effective amount of the aforesaid pharmaceutical composition to a subject in need of the treatment. In an exemplary embodiment, the effective amount ranges from 0.001-1,000 mg of the dimer per dose.

In yet another aspect of this invention, an isolated polypeptide comprising an amino acid sequence of SEQ ID NO: 2-7 is provided. In one embodiment, a pharmaceutical composition is provided comprising as its active ingredient, a purified polypeptide comprising an amino acid sequence of SEQ ID NO: 2-7. In an exemplary embodiment, the polypeptide has a purity of 90-100%; in another exemplary embodiment, the polypeptide has a purity of 95-100%; in yet another exemplary embodiment, the polypeptide has a purity of 99-100%.

In one exemplary embodiment in this specific aspect, a method to treat a neurological disorder comprising administrating an effective amount of the aforesaid pharmaceutical composition to a subject in need of the treatment. In yet another exemplary embodiment, disease is selected from a group consisting of: stroke, spinal injury, and neurological disorders accompanied with blood brain barrier injury.

In another exemplary embodiment in this specific aspect, a method of activating STAT3 in neural cells comprising administering an effective amount of the aforesaid pharmaceutical composition to a subject in need of the treatment.

In another aspect of this invention, a method for manufacture of a G-CSF dimer is provided which comprises the steps of:

a). transforming mammalian cells with an expression vector comprising a DNA sequence encoding a G-CSF-Fc complex comprising a nucleotide sequence selected from a group consisting of SEQ ID NO: 9-10;

b). culturing the transformed mammalian cells under conditions sufficient for expressing the G-CSF-Fc complexes and the G-CSF dimers; and isolating and purifying the G-CSF dimer obtained from step (b);

wherein the G-CSF dimer comprises two G-CSF-Fc complexes in which each G-CSF-Fc complex comprises an amino acid sequence selected from a group consisting of SEQ ID NO: 2-7.

In yet another aspect of this invention, a method for manufacture of an isolated polypeptide is provided which comprises the steps of:

a). transforming mammalian cells with an expression vector comprising a DNA sequence encoding the polypeptide comprising a nucleotide sequence selected from a group consisting of SEQ ID NO: 9-10;

b). culturing the transformed mammalian cells under conditions sufficient for expressing the polypeptide; and isolating and purifying the polypeptide obtained from step (b);

wherein the polypeptide comprises an amino acid sequence selected from a group consisting of SEQ ID NO: 2-7.

In this specific embodiment, the G-CSF dimer has a G-CSF monomer (amino acid residues 1-174) connected to another G-CSF monomer (amino acid residues 191-364) by a linker (amino acid residues 175-190).

Figure 2A:
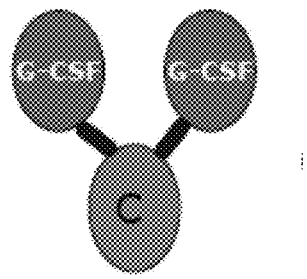
Figure 2B:
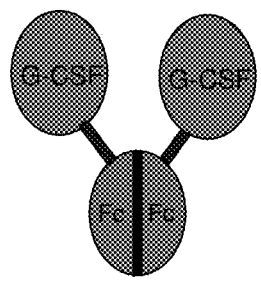

FIGS. 2a and 2b are illustration of the structure of a G-CSF dimer according to one embodiment of the present invention. In the figure, "-" represents the linker and the oval-shaped object labeled with "G-CSF" represents a G-CSF monomer. The oval-shaped object labeled with "C" represents a carrier protein in which the G-CSF monomer is disposed at the N-terminal of the carrier protein. The oval-shaped object labeled with "Fc" represents a Fc fragment of the human IgG2.

Figure 3A:
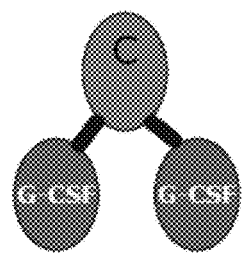
Figure 3B:
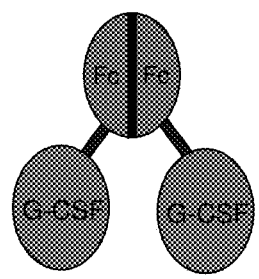

FIGS. 3a and 3b are illustration of the structure of a G-CSF dimer with amino acid according to one embodiment of the present invention. In the figure, "-" represents the linker and the oval-shaped object labeled with "G-CSF" represents a G-CSF monomer. The oval-shaped object labeled with "C" represents a carrier protein in which the G-CSF monomer is disposed at the C-terminal of the carrier protein. The oval-shaped object labeled with "Fc" represents a Fc fragment of the human IgG2.

Figure 4:
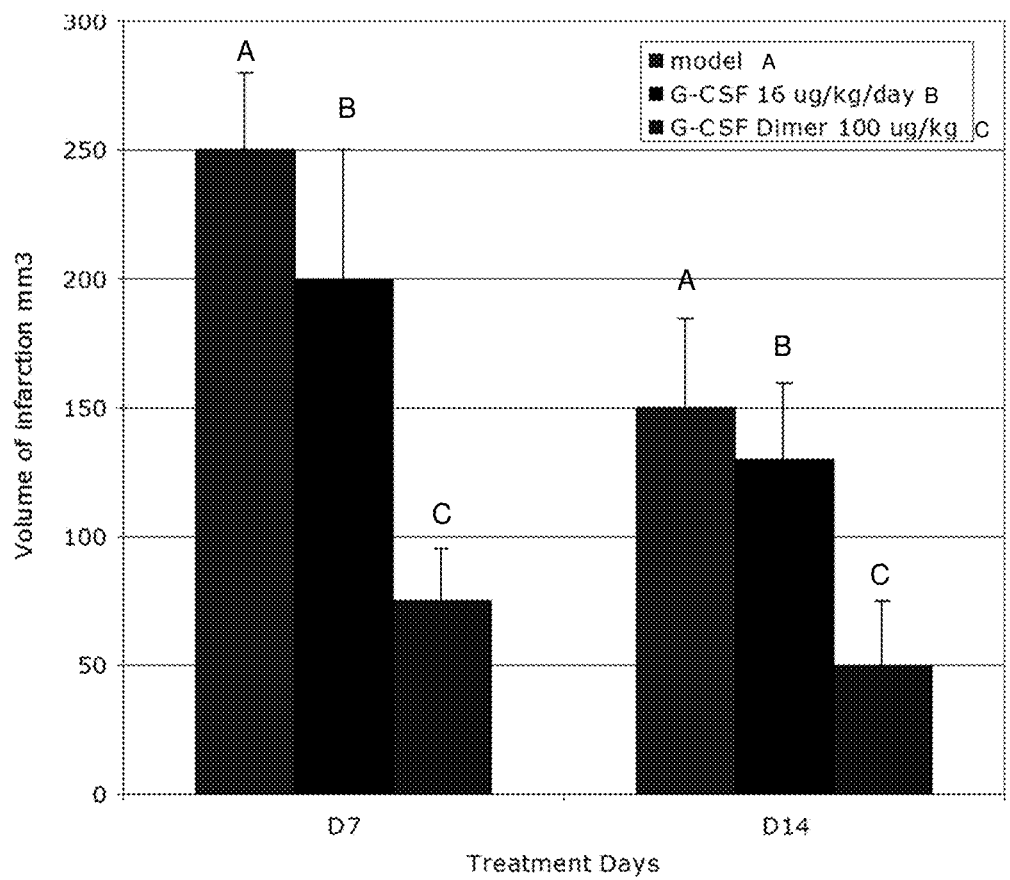
Figure 6:
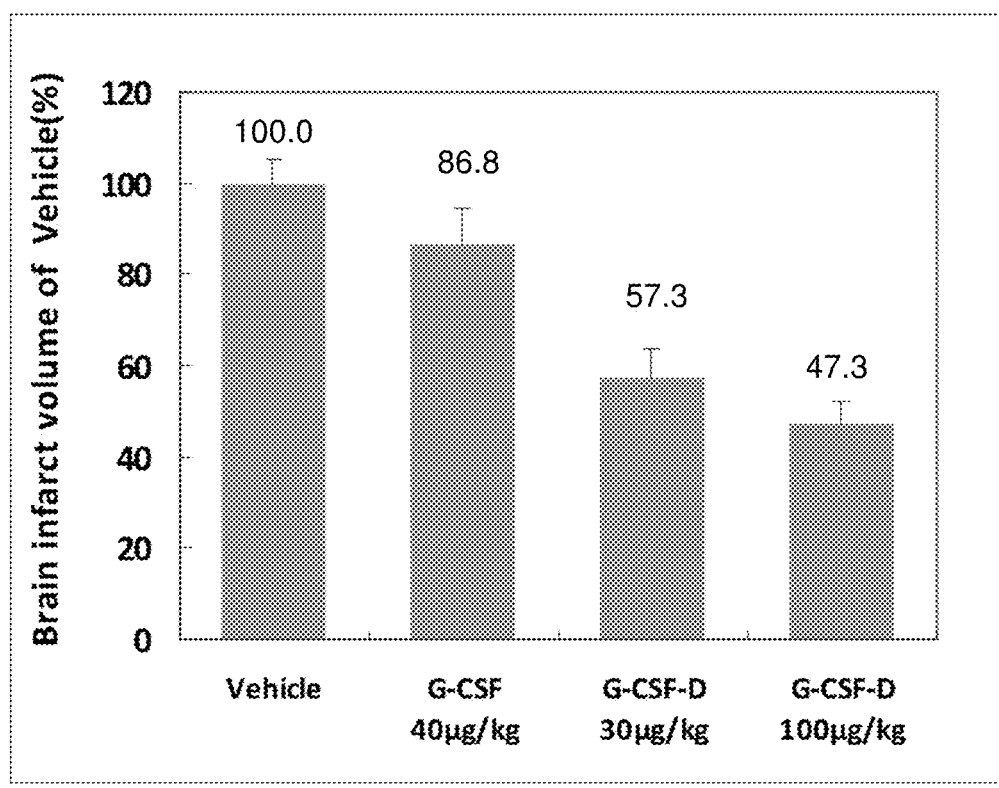

FIGS. 4, 6 show the clinical efficacy of the G-CSF dimer according to one embodiment of the present invention from the study of focal cerebral ischemia animal model.

Figure 5:
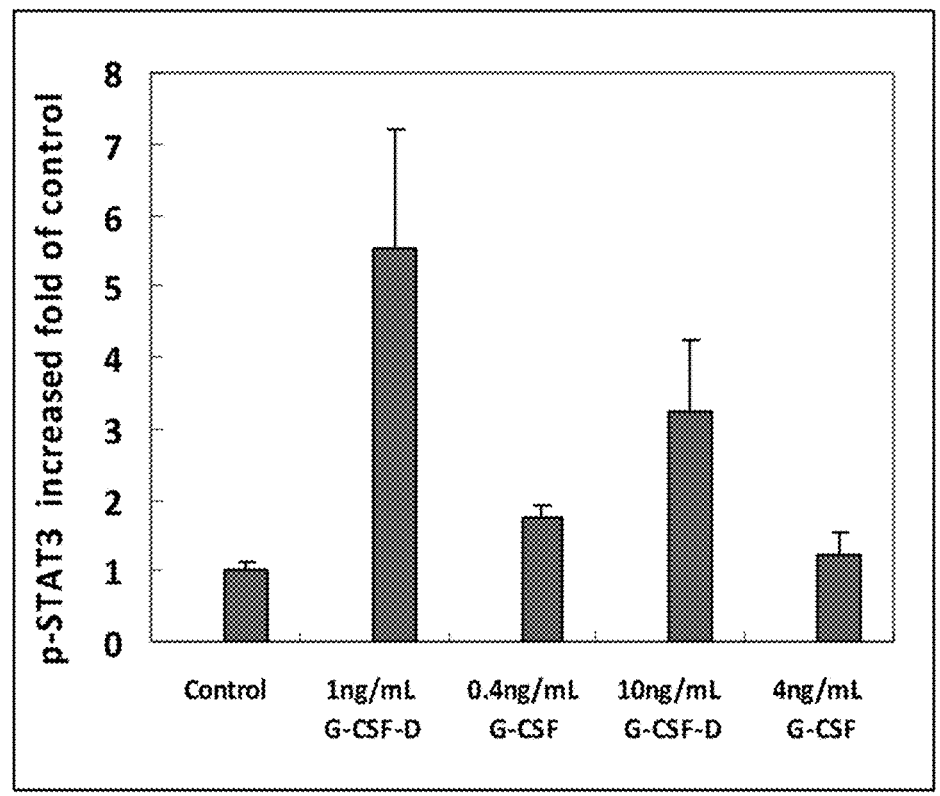

FIG. 5 shows the effectiveness to activate STAT3 in vitro by G-CSF dimer according to one embodiment of the present invention.

DETAILED DESCRIPTION OF THE PREFERRED EMBODIMENTS

Upon an extensive and thorough research, the inventors have successfully created a novel G-CSF dimer as described herein. This novel G-CSF dimer is shown to prolong in vivo half-life thereof, improve pharmacokinetic properties of the drug thereof, reduce the drug administration frequency, enhance in vivo drug activity and promote rehabilitation of recovery of neurological function. The G-CSF dimer is also shown to exhibit significant STAT3 activation compared to the monomer G-CSF at equal G-CSF molar ratio, thus to enhance the bioactivity of the drug thereof, improve the therapeutic outcome of neural injuries. The aforesaid features will be further described in the examples below.

G-CSF Dimer

Figure 1:
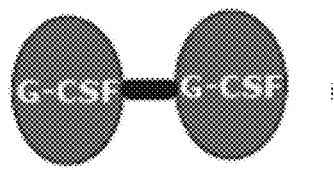
FIG. 1 is an illustration of the structure of a G-CSF dimer with amino acid sequence as shown in SEQ ID NO:1 according to one embodiment of the present invention. In the figure, "-" represents the linker and the oval-shaped object labeled with "G-CSF" represents a G-CSF monomer.

The first embodiment of the present invention is a G-CSF dimer represented by the aforesaid formula (I) and the structural illustration thereof is shown in FIGS. 1-3. Carrier protein comprises Fc fragment of human IgG1, IgG2, IgG3, IgG4, and human albumin.

In one preferred embodiment, G-CSF can be disposed at the C-terminal or N-terminal of the carrier protein as shown in FIGS. 2-3.

As used herein and in the claims, "linker" refers to a molecule that is capable of connecting two monomer polypeptides together such that the resulting compound retains the biological activity or has an improved biological activity of the monomer polypeptide.

In a preferred embodiment, "linker" refers to an organic linker or a sequence of peptide bonded amino acids that joins or links by peptide bonds two amino acid that joins or links by peptide bonds two amino acid sequences or polypeptide domains that are not joined by peptide bonds in nature. A linker sequence is encoded in frame on a polynucleotide between the sequences encoding the two polypeptide domains joined by the linker.

In another preferred embodiment, "linker" can also refer to a short peptide for connecting the two G-CSF monomers sandwiching the short peptide. There is no special restriction on the length of the linker. A linker is usually 5-50 amino acid residues in length and in general, a linker does not affect or significantly affect the proper fold and conformation formed by the configuration of the two G-CSF monomers.

A list of examples of linkers include: an organic linker, a short peptide comprising 3-50 amino acids, and a polypeptide represented by the aforesaid formula (II).

In one preferred embodiment, the organic linker can be oxymethylphenylacetamidomethyl (PAM) resin, 4-oxymethyl phenylacetamidomethyl resin, chloromethyl polystyrene resin, or any combination thereof with sufficiently little steric hindrance for not affecting or significantly affecting the proper fold and conformation formed by the configuration of the two G-CSF monomers.

In another preferred embodiment, the linker comprises amino acids with a relatively small structural conformation for not for not affecting or significantly affecting the proper fold and conformation formed by the configuration of the two G-CSF monomers, such as glysine, alanine, proline, etc.

In yet another preferred embodiment, the linker contains amino acid sequence selected from a group consisting of:

(a). an amino acid sequence with 3-15 amino acid residues formed by hydrophobic amino acids glycine (Gly) or proline (Pro), such as Gly-Pro-Gly-Pro-Gly-Pro;

(b). an amino acid sequence encoded by multiple cloning sites. Such sequence usually contains 5-20 amino acid residues; in a preferred embodiment, such sequence contains 10-20 amino acid residues;

(c). an amino acid sequence comprising protein(s) not from G-CSF monomer, such as an amino acid sequence of IgG or albumin;

(d). an amino acid sequence comprising any combination of (a), (b), and (c) above.

In one preferred embodiment, the linker has the sequence of GSGGGSGGGGSGGGGS (i.e. 175-190 amino acid residues of SEQ ID NO:1). In another preferred embodiment, the linker has the sequence of ASTKGP (i.e. 175-180 amino acid residues of SEQ ID NO:4).

In a further preferred embodiment, an amino acid sequence not affecting the biological activity of G-CSF monomer can be added to the N-terminal or C-terminal of the G-CSF dimer. In a preferred embodiment, such appended amino acid sequence is beneficial to expression (e.g. signal peptide), purification (e.g. 6×His sequence, the cleavage site of *Saccharomyces cerevisiae* α-factor signal peptide), or enhancement of biological activity of the G-CSF dimer.

Sequence Listing

SEQ ID NO:1 represents a G-CSF dimer as shown in FIG. 1 comprising a G-CSF monomer (amino acid residues 1-174) connected to another G-CSF monomer (amino acid residues 191-364) by a linker (amino acid residues 175-190).

SEQ ID NO:2 represents a G-CSF-Fc complex as component for making the G-CSF dimer as shown in FIGS. 2a and 2b, comprising a G-CSF monomer (amino acid residues 1-174), a Fc fragment of human IgG2 (amino acid residues 191-418), and a peptide connecting said G-CSF monomer and said Fc fragment (amino acid residues 175-190). The dimer is formed through the pairing of the Fc fragments contained in each of the two G-CSF-Fc complexes. In one embodiment, the Fc fragments are paired via a plurality of disulfide bonds disposed therebetween; in yet another embodiment, the number of the disulfide bonds disposed therebetween is 2 or 4.

SEQ ID NO:3 represents a G-CSF-Fc complex as component for making the G-CSF dimer as shown in FIGS. 3a and 3b, comprising a G-CSF monomer (amino acid residues 245-418), a Fc fragment of human IgG2 (amino acid residues 1-228), and a peptide connecting said G-CSF monomer and said Fc fragment (amino acid residues 229-244). The dimer is formed through the pairing of the Fc fragments contained in each of the two G-CSF-Fc complexes. In one embodiment, the Fc fragments are paired via a plurality of disulfide bonds disposed therebetween; in yet another embodiment, the number of the disulfide bonds disposed therebetween is 2 or 4.

SEQ ID NO:4 represents a G-CSF-Fc complex as component for making the G-CSF dimer as shown in FIGS. 2a and 2b comprising a G-CSF monomer (amino acid residues 1-174), a Fc fragment of human IgG2 (amino acid residues 181-403), and a peptide connecting said G-CSF monomer and said Fc fragment (amino acid residues 175-180). On comparing with SEQ ID NO:2, SEQ ID NO:4 has a shorter peptide connecting said G-CSF monomer and said Fc fragment (with ten less amino acid residues). Also, a short sequence of ERKCC is deleted in SEQ ID NO4, by which two disulfide bonds are removed to result in reducing the possibility of mismatch of hinge. The dimer is formed through the pairing of the Fc fragments contained in each of the two G-CSF-Fc complexes. In one embodiment, the Fc fragments are paired via a plurality of disulfide bonds disposed therebetween; in yet another embodiment, the number of the disulfide bonds disposed therebetween is 2 or 4.

SEQ ID NO:5 represents a G-CSF-Fc complex as component for making the G-CSF dimer as shown in FIGS. 3a and 3b, comprising a G-CSF monomer (amino acid residues 230-403), a Fc fragment of human IgG2 (amino acid residues 1-223), and a peptide connecting said G-CSF monomer and said Fc fragment (amino acid residues 224-229). On comparing with SEQ ID NO:3, SEQ ID NO:5 has a shorter peptide connecting said G-CSF monomer and said Fc fragment (with ten less amino acid residues). Also, a short sequence of ERKCC is deleted in SEQ ID NO:5, by which two disulfide bonds are removed to result in reducing the possibility of mismatch of hinge. The dimer is formed through the pairing of the Fc fragments contained in each of the two G-CSF-Fc complexes. In one embodiment, the Fc fragments are paired via a plurality of disulfide bonds disposed therebetween; in yet another embodiment, the number of the disulfide bonds disposed therebetween is 2 or 4.

SEQ ID NO:6 represents a G-CSF-Fc complex as component for making the G-CSF dimer as shown in FIGS. 2a and 2b comprising a G-CSF monomer (amino acid residues 1-174), a Fc fragment of human IgG2 (amino acid residues 191-413), and a peptide connecting said G-CSF monomer and said Fc fragment (amino acid residues 175-190). On comparing with SEQ ID NO:2, a short sequence ERKCC is deleted in SEQ ID NO:6, by which two disulfide bonds are removed to result in reducing the possibility of mismatch of hinge. The dimer is formed through the pairing of the Fc fragments contained in each of the two G-CSF-Fc complexes. In one embodiment, the Fc fragments are paired via a plurality of disulfide bonds disposed therebetween; in yet another embodiment, the number of the disulfide bonds disposed therebetween is 2 or 4.

SEQ ID NO:7 represents a G-CSF-Fc complex as component for making the G-CSF dimer as shown in FIGS. 3a and 3b, comprising a G-CSF monomer (amino acid residues 240-413), a Fc fragment of human IgG2 (amino acid residues 1-223), and a peptide connecting said G-CSF monomer and said Fc fragment (amino acid residues 224-239). On comparing with SEQ ID NO:3, a short sequence ERKCC is deleted in SEQ ID NO:7, by which two disulfide bonds are removed to result in reducing the possibility of mismatch of hinge. The dimer is formed through the pairing of the Fc fragments contained in each of the two G-CSF-Fc complexes. In one embodiment, the Fc fragments are paired via a plurality of disulfide bonds disposed therebetween; in yet another embodiment, the number of the disulfide bonds disposed therebetween is 2 or 4.

SEQ ID NO:8 represents a G-CSF monomer molecule.

SEQ ID NO:9 represents the DNA sequences of SEQ ID NO:2.

SEQ ID NO:10 represents the DNA sequences of SEQ ID NO:6.

Preparation Method

The encoding of the DNA sequences of the G-CSF dimer or fusion protein of the present invention can be entirely artificially synthesized. Alternatively, the encoded DNA sequences of the first G-CSF monomer and/or the second G-CSF monomer can be obtained by PCR amplification or synthesis and joined together to form the encoded DNA sequence of the G-CSF dimer or fusion protein of the present invention.

In order to enhance the expression volume of the host cells, modification can be performed on the encoded sequence of G-CSF dimer. For example, codon bias of host cells can be used to eliminate sequences that are not beneficial to transcription and translation. In a preferred embodiment, codon bias of yeast cells or mammalian cells can be used together with DNA software for detecting genes of DNA dimer, to eliminate sequences that are not beneficial to transcription and translation. In one preferred embodiment, the eliminated sequences can be intron cutting site, transcription terminating sequence, etc.

After the encoded DNA sequence of the novel fusion protein of the present invention is obtained, it is first inserted into an appropriate expression carrier, followed by an appropriate host cell. Finally, the transformed host cell is cultivated and purified to obtain the novel fusion protein of the present invention. The DNA sequences of SEQ ID NO:2 and 6 are shown in SEQ ID NO: 9 and 10 respectively.

As used herein and in the claims, "carrier" refers to plasmid, cosmid, expression vehicle, cloning vector, virus vector, etc.

In this invention, carrier known in the art, such as carriers available in the market, can be used. For example, with the use of carrier obtained from the market, encoded nucleotide sequence of the novel fusion protein of the present invention is operationally connected to the expressing and controlling sequence to form the protein-expressing carrier.

As used herein and in the claims, "operationally connected" refers to a scenario that some parts of a linear DNA sequence can affect the biological activity of other parts of the same linear DNA sequence. For instance, if signal DNA is used as the expression of a precursor and participates in secretion of polypeptides, said signal DNA (secretion leader sequence) is "operationally connected" to said polypeptides. If a promoter controls sequence transcription, the promoter is "operationally connected" to the encoded sequence. If a ribosome binding site is situated at a position where translation thereof is made possible, said ribosome binding site is "operationally connected" to the encoded sequence. In general, "operationally connected" means that the residues of concern are in proximity; for secretion leader sequence, "operationally connected" refers to proximity within the reading frame.

As used herein and in the claims, "host cells" refers to both prokaryotic cells and eukaryotic cells. Prokaryotic host cells commonly used include *E. coli, B. subtilis*, etc. Eukaryotic host cells commonly used include yeast cells, insect cells, mammalian cells, etc. In a preferred embodiment, the host cells used are eukaryotic cells; in another preferred embodiment, the host cells used are mammalian cells.

After the transformed host cells are obtained, they can be cultivated under an environment suitable to express the fusion protein of the present invention for expressing the fusion protein. The expressed fusion protein is then separated.

As used herein and in the claims, "neurological disorders or neurological diseases" refers to stroke, spinal injury, and neurological disorders accompanied with blood brain barrier injury.

Pharmaceutical Composition and Method of Administration Thereof

Since the G-CSF dimer of the present invention has an excellent serum half-life, the G-CSF dimer and a pharmaceutical composition comprising the G-CSF dimer as the main active ingredient can be used for treating disease associated with neural injury, and for protecting neurons. In a preferred embodiment, the disease associated with neural injury is selected from a group consisting of: stroke, spinal injury, and neurological disorders accompanied with blood brain barrier injury.

The pharmaceutical composition of the present invention comprises a safe and effective amount of said G-CSF dimer and a pharmaceutically acceptable excipient or carrier. "Safe and effective amount" refers to an amount of a compound sufficient to substantially improve the condition of the patient in need thereof without causing serious side-effects. In general, the pharmaceutical composition comprises 0.001-1,000 mg of G-CSF dimer per dose; in a preferred embodiment, the pharmaceutical composition comprises 0.05-300 mg of G-CSF dimer per dose; in another preferred embodiment, the pharmaceutical composition comprises 0.5-200 mg of G-CSF dimer per dose.

The compound of the present invention and its pharmaceutically acceptable salts can be manufactured into different formulations, which comprises a safe and effective amount of said G-CSF dimer or its pharmaceutically acceptable salts and a pharmaceutically acceptable excipient or carrier. "Safe and effective amount" refers to an amount of a compound sufficient to substantially improve the condition of the patient in need thereof without causing serious side-effects. The safe and effective amount of a compound is determined according to the age, condition, course of treatment, etc. of the patient in treatment.

"Pharmaceutically acceptable excipient or carrier" refers to solid or liquid filling or gelatin materials with one or different kinds of compatibility which are suitable to be used in human with sufficient purity and sufficiently low toxicity. "Compatibility" refers to the ability of each ingredient of the composition to mutually blend with the compound of the present invention and the mutual blending ability therebetween, without substantially decreasing the clinical efficacy of the compound. Some of the examples of pharmaceutically acceptable excipient or carrier include cellulose and its derivatives (e.g. sodium carboxymethylcellulose, sodium ethylcellulose, cellulose acetate, etc), gelatin, speckstone, solid lubricating agent (e.g. stearic acid, magnesium stearate), calcium sulphate, plant oil (e.g. pea oil, sesame oil, peanut oil, olive oil, etc.), polyols (e.g. propylene glycol, glycerol, mannitol, sorbitol, etc.), emulsifier (e.g. Tween®), wetting agent (e.g sodium lauryl sulfate), colorant, flavoring agent, stabilizer, anti-oxidant, antiseptic, pyrogen-free water, etc.

Route of administration of the G-CSF dimer of the present invention comprises oral administration, rectal administration, parenteral administration (intravenous, intramuscular, or subcutaneous), and partial administration.

Solid form for oral administration comprises capsules, tablets, pills, powder, and granules. In these solid forms, active compound is mixed with at least one of the conventionally inert excipients (or carriers), such as sodium citrate, dicalcium phosphate, or any of the following ingredients: (a) filing or bulking agent, e.g. starch, lactose, sucrose, glucose, mannitol, and silicic acid; (b) adhesion agent, e.g. carboxymethylcellulose, alginate, gelatin, polyvinyl pyrrolidone, sucrose, and acacia; (c) humectants, e.g. glycerol; (d) disintegrating agent, e.g. agar, calcium carbonate, potato starch or cassava starch, alginic acid, compounded silicate, and sodium carbonate; (e) buffering agent, e.g. paraffin wax; (f) absorption accelerating agent, e.g. quaternary amine compound; (g) wetting agent, e.g. cetanol and glycerin monostearate; (h) absorbent, e.g. bolus alba; and (i). lubricating agent, e.g. speckstone, calcium stearate, sodium stearate, solid polyethylene glycol, sodium lauryl sulfate, or any mixture thereof. Capsules, tablets, and pills can also comprise buffering agent.

Solid forms such as tablets, sugar pill, capsules, pills, and granules can be prepared with coating and core-shell materials, such as casing and other materials known in the art. These materials comprise opacifying agent and the active compound or compound in such composition can be released in a delayed fashion that the release is done in certain part of the alimentary canal. Embedding component such as polymer materials and wax materials can be used. If desired, active compounds can be mixed with one or more of the above-described excipients to formulate a micro capsule form.

Liquid forms for oral administration comprise pharmaceutically acceptable emulsion, solution, suspension, syrup, or tincture. Apart from active compounds, liquid forms also comprise inert diluents conventionally used in the art such as water or other solvent, solubilizing agent and emulsifier such as ethanol, isopropanol, carbonate acetate, ethyl acetate, propan-2-ol, 1,3-butan-2-ol, dimethylfomamide, and oil, in particular cotton oil, peanut oil, castor oil, olive oil, maize embryo oil, and sesame oil or any mixture thereof.

Apart from the inert diluents, the compound can also comprise additives, such as wetting agent, emulsifying agent, suspending agent, sweetening agent, correctives, and spices.

Apart from active compounds, suspension can also comprise suspending agent, such as ethoxyl isostearic alcohol, polyoxyethylene sorbitol, sorbitan, microcrystalline cellulose, aluminium methoxide, agar, or any mixture thereof.

Compounds used for parenteral administration can also comprise physiologically acceptable sterile water or anhydrous solution, dispersion solution, suspension, or emulsion, and sterile powder that can be re-dissolved into sterile injectable solution or dispersion solution. Appropriate hydrated or anhydrous carriers, diluting agent, solvent, or excipient comprises water, ethanol, polyols, and its appropriate mixtures thereof.

Forms of the G-CSF dimer of the present invention used for partial administration comprise ointment, powder, patch, sprayer, and inhalant. Under sterile conditions, active components can be mixed with physiologically acceptable carrier and any antiseptic, buffering agent, or may be propellant if desired.

The G-CSF dimer of the present invention can be solely administrated or be administrated in conjunction with any pharmaceutically acceptable compounds.

On using the pharmaceutical composition, a safe and effective of the amount of the G-CSF dimer of the present invention is administrated to a mammal (e.g. human) in use thereof in which the dosage administrated is a pharmaceutically acceptable effective administration dosage. For a human of 60 kg, the administration dosage is usually 0.01-300 mg; in a preferred embodiment, the administration dosage is 0.5-100 mg. In determination of the actual dosage, factors known in the art such as administration route, patients' condition, etc. have to be considered.

There are many advantages of the G-CSF dimer of the present invention which includes but not limited to:

1. A longer in vivo biological half-life.
2. A better biological activity in activating STAT3 in neural cells.
3. A substantial clinical efficacy in a single or two-time injection in ischemic animal model.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein. Further, for the embodiments in which details of the experimental methods are not described, such methods are carried out according to conventional conditions such as those described in Sambrook et al. Molecular Cloning: A Laboratory Manual (New York: Cold Spring Harbor Laboratory Pres, 1989), or suggested by the manufacturers.

EXAMPLES

The G-CSF dimer of the present invention having amino acid sequence of SEQ ID NO:1 or comprising G-CSF-Fc complexes with amino acid sequence SEQ ID NO: 2-7 with the structure thereof described in FIGS. 1-3 is prepared and purified by conventional methods. Exemplary methods thereof are described in Examples 1-3 below.

Example 1

Construction of a Mammalian Vector Expressing rhG-CSF Dimer

The full length DNA sequence containing human G-CSF, a linker peptide, and a Fc fragment of human immunoglobulin (IgG2) was synthesized. At the 5' end, sequences containing a restriction enzyme, Hind III, site, Kozak sequence, and signal peptide were introduced. At the 3' end, a sequence containing EcoRI site was introduced. The full length G-CSF dimer DNA sequence was cloned into pUC19 to result in pG-CSF-Fc. The plasmid was amplified in *E. Coli* TG1, and digested with Hind III and EcoRI, and subcloned into pcDNA3 (Invitrogen) vector to result in expression vector pEX-G-CSF-Fc. pEX-G-CSF-Fc was linearized and transfected into CHO cells by electroporation. The transfected cells were selected in selecting media and cloned. The protein levels of individual clones were measured by ELISA. The clones with the highest G-CSF-Fc dimer expression levels were frozen to generate cell bank and used for recombinant protein generation.

As an example for illustration, the aforesaid full length DNA sequence containing human G-CSF, a linker peptide, and a Fc fragment of human immunoglobulin (IgG2) has a corresponding amino acid sequence of SEQ ID NO: 2-7. As such, according to the steps as afore-described, the resulting expression vector pEX-G-CSF-Fc comprising a corresponding amino acid sequence of SEQ ID NO: 2-7 was linearized and transfected into CHO cells by electroporation. The transfected cells were selected in selecting media in which a mixture of G-CSF-Fc monomers and G-CSF-Fc dimers were expressed. The protein levels of individual clones were measured by ELISA. The clones with G-CSF-Fc dimer expression were first selected and those with the highest G-CSF-Fc dimer expression levels were frozen to generate cell bank and used for recombinant protein generation.

Example 2

Production of rhG-CSF Dimer Protein in Mammalian Cells

One vial of cells ($\sim 1 \times 10^7$ cells/ml) from the cell bank was thawed and seeded in 10 mL basal medium in a 10 cm Petri dish and incubated at 37° C., 5% $CO_2$ for approximately 24 hrs.

The seeding expansion: The culture was sequentially expanded in shaking flasks in 3-4 times in volume (eg. from 10 mL to 30-40 mL). When the cell density reached $1.0$-$1.5 \times 10^6$ cells/mL with viability ≥90%, the culture volume reached 300-400 mL. The shaking flasks were incubated at 120 rpm 37° C., 5% $CO_2$.

Stage one of culture expansion in bioreactor (3 L-10 L): When the cell density in the seeding expansion reached 300-400 mL at $1.0$-$3.0 \times 10^6$ cells/mL with viability ≥90%, the seeding expanded culture was aseptically transferred to a 3-10 L bioreactor containing basal medium, with the culture control conditions at 37° C., pH of 6.8, dissolved Oxygen at approximately 50% and stirring speed at 65-100 rpm.

Stage two of culture expansion in bioreactor (30-100 L): When the cell density in the 3.0-10 L bioreactor reached $1.0$-$3.0 \times 10^6$ cells/ml with viability ≥90%, the culture was aseptically transferred to 30-100 L bioreactor containing a basal medium, with the culture control conditions at 37° C., pH of 6.8, dissolved Oxygen at approximately 50% and stirring speed at 65-100 rpm. The culture was fed at 12 to 48 hrs to control the glucose level at or below 1 g/L with the addition of fed-batch medium before harvest.

Example 3

Purification of Recombinant Human G-CSF Dimer Protein

Purification process of G-CSF dimer protein was carried out by affinity chromatography, since the G-CSF dimer protein contains a human Fc fragment capable of binding to protein A. Supernatant harvested from bioreactor contains G-CSF-Fc multi-mer (or aggregate), dimer, and G-CSF-Fc complex and metabolites. After being harvested from the bioreactor culture, the cell culture supernatant was obtained by filtration, followed by stepwise purification at ambient temperature using a series of chromatography columns to obtain the purified recombinant product. For example, a typical rProtein A Sepharose FF (GE Healthcare, cat#17-1279-04) column with elution buffer containing 50 mM critic acid/sodium citrate and 0.2M NaCl with pH 3.7-3.8 is used, resulting in >90% pure G-CSF dimer protein by reverse phase HPLC analysis. Additional chromatography steps were performed using Capto Adhere column in elution buffer containing 50 mM NaAc/HAC and 0.2 M NaCl with pH 4.5-5.0, followed by SP Sepharose FF (GE Heathcare Cat #17-0729-04). Sample buffer used was 50 mM NaAC/HAC (pH4.5-5.0), whereas equilibrium buffer was 10 mM PB (pH $6.0 \pm 0.1$). Elute buffer used was 10 mM PB and 0.2M NaCl (pH $7.2 \pm 0.1$) with flow rate of 10-200 cm/hr depending on the size of the column Additional processes involved viral activation at low pH, filtration, and buffer balance by dialysis.

The purity of the G-CSF dimer protein was >95% by reverse phase HPLC, with estimated molecular weight of $47 \pm 5$ Kd by reduced SDS-PAGE analysis. The G-CSF dimer protein was glycosylated with oligosaccharide of 2-10% of the total molecular weight. The isoelectric point of the protein was between pH 5.8 to pH 6.8. The maximum UV absorbing wavelength was at 280 nM.

The G-CSF dimer fusion protein exhibited the following in vitro biological activities including stimulation of the proliferation and the activation of STAT3 in M-NSF-60 cell lines in a dose-dependent manner. The ED50 for STAT3 activation and proliferation in M-NSF-60 cells was between 0.1-10 ng/mL. The proliferation of M-NFS-60 cells stimulated by G-CSF dimer could be neutralized by the anti-human G-CSF antibody. In addition, the G-CSF dimer protein was able to activate STAT3 in primary neuron cells. The G-CSF dimer fusion protein exhibited the following in vivo biological activities including rapid increase of cell counts in white blood cells (WBC), neutrophils in normal or neutropenic animals including mice, rats, and monkeys. The G-CSF dimer protein was also able to activate STAT3 in primary neurons in vitro and to reduce the infarct volume of brain in the acute ischemic stroke model in rats.

Example 4

In vivo Half-Life of G-CSF Dimer

Rats received a single dose of 100 μg/kg of G-CSF dimer of the present invention composed of two G-CSF-Fc complexes (SEQ ID NO: 3) by subcutaneous injection. The pharmacokinetic parameters were calculated and listed in Table 1 below.

TABLE 1

| Parameter (n = 6) | Unit | Average Value | SD |
| --- | --- | --- | --- |
| $AUC_{(0-t)}$ | ng/mL * h | 4234.8 | 640.3 |
| $MRT_{(0-t)}$ | h | 21.6 | 1.4 |
| $t_{(1/2)}$ | h | 7.7 | 1.2 |
| Clz/F | L/h/kg | 0.024 | 0.003 |
| $C_{max}$ | ng/mL | 162.2 | 30.2 |

From the above Table 1, it can be seen that the in vivo half-life of G-CSF dimer in rats is about 7.7 hours, whereas the in vivo half-life of G-CSF monomer is about 2 hours.

Example 5

Pharmacokinetic Properties of G-CSF Dimer in Human

Healthy male subjects received an ascending single dose of 30, 60, 120, 240 μg/kg of G-CSF dimer (G-CSF-D; composed of two G-CSF-Fc complexes (SEQ ID NO: 6) by subcutaneous injection. A total of 24 healthy male subjects were enrolled and assigned to 4 sequential single dose cohorts of G-CSF-D (30, 60, 120 and 240 μg/kg).

Blood samples were collected before drug administration and at 0.5, 1, 2, 4, 8, 16, 24, 36, 48, 72, 96 hours, Day 6 (120 hrs), 7, 9, 11, 13, and 15 after dosing. Serum was separated and stored below −70° C. The serum concentrations of G-CSF-D were measured by an enzyme-linked immunoassay (ELISA, Quantikine human G-CSF ELISA kit, R&D System, Inc. Minneapolis, Minn., Cat: PDCS50).

The pharmacokinetic parameters were calculated using the standard non-compartmental analytical procedures (WinNonlin v 5.2, Pharsight Corporation, USA). The actual times of sample collection were used in the calculations of pharmacokinetic parameters. $C_{max}$ (the maximum observed plasma concentration over the sampling period) and $T_{max}$ (the time at which Cmax occurred) were taken directly from the data. The elimination rate constant, Kel ($hr^{-1}$) was determined by linear regression of a minimum of 3 points. Area under the plasma concentration versus time curve (AUC) was determined by the linear trapezoidal rule, where $AUC_{last}$ was the AUC from time zero until the last concentration point. $AUC_{(0-inf)}$ was the $AUC_{last}$ and the last concentration point divided by Kel. Half-life ($t_{1/2}$) was determined according to $t_{1/2}$=0.693/Kel where possible. Apparent clearance (CL) was calculated as dose/$AUC_{(0-inf)}$.

The results as shown in Table 2 illustrated that the G-CSF dimer had $t_{1/2}$ between 43.9 and 62.8 hrs in human, while the half-life of G-CSF monomer had $t_{1/2}$ of approximately 3.5 hrs. The G-CSF dimer thus has significantly improved pharmacokinetic properties by at least 12 folds.

TABLE 2

| Parameter (n = 6) | 30 μg/kg | 60 μg/kg | 120 μg/kg | 240 μg/kg |
| --- | --- | --- | --- | --- |
| $C_{max}$ (ng/mL) | 21.3 (10.3) | 44.6 (17.7) | 219.9 (76.6) | 759 (160) |
| $T_{max}$ (h, median & range) | 8 (8-16) | 8 (8-16) | 16 (16-36) | 36 (36) |
| $t_{1/2}$ (h) | 43.9 (4.3) | 56.1 (23.3) | 59.3 (23.5) | 62.8 (10.8) |
| $AUC_{(0-inf)}$ (ng · h/mL) | 778 (213) | 1847 (686) | 8349 (2769) | 46664 (17258) |
| CL/F (mL/h/kg) | 41.4 (12.8) | 36.8 (14.6) | 18.5 (7.7) | 5.7 (2.0) |

Mean (SD)

Example 6

Activation of Signal Transducer and Activator of Transcription 3 (STAT3) by G-CSF Dimer Mice with injured or impaired brain-blood barrier can be used to show the improved bioactivity of activating pSTAT3 for G-CSF dimer. First, tested mice can be divided into different groups of: control group receiving a control, G-CSF group receiving G-CSF monomer, and G-CSF dimer group receiving G-CSF dimer. The G-CSF dimer used in this study can comprise two G-CSF-Fc complexes and the amino acid sequence for such G-CSF-Fc complex can be selected from any one of SEQ ID NO: 2-7. The amount of G-CSF and G-CSF dimer respectively injected into the G-CSF group and the G-CSF dimer can be determined such that both groups practically receive the equal molar ratio of the G-CSF. At the end of the study, the mice can be sacrificed and brain tissues can be harvested and lysed. The content of phosphorylated STAT3 (pSTAT3) can then be measured using conventional tool such as an ELISA kit.

On analyzing the data obtained from performing the aforesaid procedures, the G-CSF dimer group can be shown to have a stronger STAT3 activating bioactivity than the G-CSF monomer group.

Example 7

Activation of STAT3 in Primary Neurons In vitro

Fetal rat brain was harvested from female SD rats at the 17th day of gestation. The whole fetal brain was placed in D-Hanks solution on ice. Cerebral cortex was carefully removed under microscopy and cut into small pieces of approximately 1 $mm^3$. The minced cerebral cortex was digested in 10 mL of 0.125% of trypsin, at 37° C. for 15 mins. The supernatant was transferred into DMEM containing 10% FBS with pipetting for a few times to stop the trypsin digestion. The cells were spun down and re-suspended in neuron culture basal medium (Invitrogen, Cat 21103049) and B27 (Invitrogen, Cat 17504044) without serum in 12-well plate with $5 \times 10^5$/well, and incubated at 37° C., 5% $CO_2$ for 8 days. The media was replaced once every two days.

The primary neuron cells after 8 days of culture were treated with carrier control, G-CSF, or G-CSF dimer composed of two G-CSF-Fc complexes (SEQ ID NO: 6) at equal molar of G-CSF concentration for 15 mins The cells were then washed twice with PBS and lysed with lysis buffer containing 20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM Na$_3$VO$_4$, 1 μg/ml leupeptin, 1 mM PMSF (Invitrogen, Cat 9803). The protein concentration in the lysate was determined using Bradford protein assay. The content of pSTAT3 in cell lysates was measured using a STAT3 ELISA kit (Invitrogen, Cat KH00481).

Results in FIG. 5 shows that both G-CSF and G-CSF dimer (represented by G-CSF-D in FIG. 5) were able to activate pSTAT3 in primary rat neurons showing a significantly elevated pSTAT3 amount compared to that of the control cultures. At equal molar of G-CSF, the G-CSF dimer is shown to activate at least 2 folds more pSTAT3 than that activated by G-CSF monomer. Thus, G-CSF dimer has stronger STAT3 activating bioactivity than that of the G-CSF monomer.

Example 8

Clinical Efficacy of G-CSF Dimer in Focal Cerebral Ischemia Animal Model Study

Middle cerebral artery, MCA, is stroke-prone sites for human. Middle cerebral artery occlusion (MCAO) model is generally regarded as the standard animal model for studying focal cerebral ischemia in which one of the main methods is the thread occlusion of the middle cerebral artery.

Male SD rats (250-300 g) were used in this study. After anaesthetized by intraperitoneal injection of pentobarbital sodium (dosage of 50-60 mg/kg), the rats were fixed in a dorsal position. Upon incision of the right neck skin and blunt dissection of sternocleidomastoid muscle and sternohyoid muscle, right common carotid artery (CCA) and vagus nerves were exposed. CCA, external carotid artery (ECA) and its branch arteries were ligated. Internal carotid artery (ICA) was dissected until extracranial branches of the pterygopalatine artery can be observed at the tympanic bulla and then that branch was ligated at its root. Thread was prepared at the near end of ICA whereas artery clamp was placed at the far end of ICA. A small cut was incised at the ligation site of ECA (5 mm from the fork of ECA and ICA) and a nylon thread with diameter of 0.22-0.249 mm was inserted via the ECA cutting. The thread was heated prior to insertion to make the insertion end become blunt and mark for length of thread was also made. The thread was tightened and the artery clamp was released, followed by inserting the nylon thread into ICA via the fork of ECA and ICA. The nylon thread was then allowed to proceed for 17-19 mm to the starting place of anterior cerebral. MCA was then occluded to result in the focal cerebral ischemia.

The rats were divided into three groups with eight rats in each group. Rats in G-CSF dimer composed of two G-CSF-Fc complexes (SEQ ID NO: 3) group were subcutaneously injected at a dose of 100 μg/kg upon a 30-minute ischemia. G-CSF dimer was re-injected once after 72 hours of modeling. Rats in G-CSF group, received rhG-CSF daily at a dose of 16 μg/kg/day by subcutaneous injection for five consecutive days. As such, by the end of the experiment, both G-CSF dimer and G-CSF groups received the equal molar of G-CSF. Rats in solvent control group received the same dose of PBS. The nylon thread was slowly removed upon a 90-minute ischemia for all groups.

From the result in FIG. 4, at equal molar dosage, although G-CSF monomer was shown to have certain clinical efficacy, there is no statistically difference between this G-CSF group and the solvent control group. On the other hand, at equal molar dosage, G-CSF was illustrated to have significant clinical efficacy.

Example 9

Effects of G-CSF Dimer in Middle Cerebral Artery Occlusion (MCAO) in Rats

SD rats (male, 250-300 grams) were used for the study. The animals were divided into 5 groups: Vehicle (MCAO+vehicle, n=12), G-CSF dimer (G-CSF-D; composed of two G-CSF-Fc complexes (SEQ ID NO: 6)) (MCAO+G-CSF-D 30 ug/kg, n=12), G-CSF-D (MCAO+rhG-CSF D 100 ug/kg, n=12), G-CSF (MCAO+40 ug/kg, n=12), and Sham group (surgical process+vehicle, n=12). The G-CSF-D was administered subcutaneously at 0.5 hr and 48 hr after blood reperfusion. G-CSF was administered subcutaneously at 0.5, 12, 24 and 48 hr after blood reperfusion. Under anesthesia, the right common carotid artery, (CCA), internal carotid artery (ICA), and external carotid artery (ECA) were exposed through a midline incision of the neck. A commercial monofilament (silicon-coated) was used as an occluder and inserted via the ECA. The occluder was advanced into the ICA 18±0.5 mm beyond the carotid bifurcation. Mild resistance indicated that the occluder was properly lodged in the anterior cerebral artery and blocked blood flow to the middle cerebral artery (MCA). After 60 minutes, reperfusion was allowed by withdrawing the monofilament by approximately 10 mm Body temperature was kept 36.5° C. with a heading pad during the surgery process 72 hrs after surgery, the rats were re-anesthetized and decapitated. The brains were removed and coronally sectioned into 6 slices with 2-mm thickness. The brain slices were incubated for 30 minutes in a 2% solution of triphenyltetrazolium chloride (TTC) at 37° C. and fixed by immersion in a 10% buffered formalin solution. The brain slices were photographed and unstained areas were defined as infracted volume. The infracted volume was measured using Image-Pro Plus 5.1.

The results as shown in FIG. 6 illustrated that at equal molar of G-CSF ratio, the group administrated with two treatments of G-CSF dimer showed only around 54% of brain infracted volume compared to the group receiving four treatments of the G-CSF monomer. The G-CSF dimer showed superior therapeutic efficacy than the G-CSF monomer in rat stroke model.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. An isolated polypeptide comprising the amino acid sequence of any one of SEQ ID NOs:4-7.

2. The isolated polypeptide of claim 1, wherein the polypeptide comprises SEQ ID NO:4.

3. The isolated polypeptide of claim 1, wherein the polypeptide comprises SEQ ID NO:5.

4. The isolated polypeptide of claim 1, wherein the polypeptide comprises SEQ ID NO:6.

5. The isolated polypeptide of claim 1, wherein the polypeptide comprises SEQ ID NO:7.

6. A pharmaceutical composition comprising as its active ingredient, a purified polypeptide according to claim 1.

7. The pharmaceutical composition of claim 6, wherein the polypeptide comprises SEQ ID NO:4.

8. The pharmaceutical composition of claim 6, wherein the polypeptide comprises SEQ ID NO:5.

9. The pharmaceutical composition of claim 6, wherein the polypeptide comprises SEQ ID NO:6.

10. The pharmaceutical composition of claim 6, wherein the polypeptide comprises SEQ ID NO:7.

11. The pharmaceutical composition according to claim 6 wherein said polypeptide has a purity of 90-100%.

12. The pharmaceutical composition of claim 11, wherein the polypeptide comprises SEQ ID NO:4.

13. The pharmaceutical composition of claim 11, wherein the polypeptide comprises SEQ ID NO:5.

14. The pharmaceutical composition of claim 11, wherein the polypeptide comprises SEQ ID NO:6.

15. The pharmaceutical composition of claim 11, wherein the polypeptide comprises SEQ ID NO:7.

16. A method to treat stroke comprising administering an effective amount of said pharmaceutical composition of claim 6 to a subject in need of the treatment.

17. The method according to claim 16 wherein said effective amount ranges from 0.001-1,000 mg of said polypeptide per dose.

18. A method of activating STAT3 in neural cells comprising administering an effective amount of the pharmaceutical composition of claim 6 to a subject in need of the treatment.

19. The method according to claim 18 wherein said effective amount ranges from 0.001-1,000 mg of said polypeptide per dose.

* * * * *